United States Patent [19]
Zannini et al.

[11] Patent Number: 5,965,165
[45] Date of Patent: Oct. 12, 1999

[54] PROCESS FOR THE PRODUCTION OF GRANULES, AND GRANULES THUS OBTAINED

[75] Inventors: Gaetano Zannini; Domenico Boraschi, both of Biot; Dominique Juge, Valbonne; Laurence Matza, Antibes, all of France

[73] Assignee: Bionatec, Biot, France

[21] Appl. No.: 08/809,793

[22] PCT Filed: Jul. 25, 1996

[86] PCT No.: PCT/FR96/01181

§ 371 Date: Mar. 27, 1997

§ 102(e) Date: Mar. 27, 1997

[87] PCT Pub. No.: WO97/04861

PCT Pub. Date: Feb. 13, 1997

[30] Foreign Application Priority Data

Jul. 27, 1995 [FR] France ..................................... 95 09390

[51] Int. Cl.$^6$ ....................................................... A61K 9/14
[52] U.S. Cl. .......................... 424/489; 424/458; 424/497; 424/462; 424/466
[58] Field of Search ..................................... 424/489, 458, 424/426, 1.25, 462, 497, 486, 466

[56] References Cited

U.S. PATENT DOCUMENTS 5,478,564  12/1995  Wantier et al. .......................... 424/426

FOREIGN PATENT DOCUMENTS

| 0 359 230 | 3/1990 | European Pat. Off. . |
| 0 600 775 | 6/1994 | European Pat. Off. . |
| 2 657 255 | 7/1991 | France . |
| 2 163 348 | 2/1986 | United Kingdom . |
| WO 93/00991 | 1/1993 | WIPO . |
| WO 94/24994 | 10/1994 | WIPO . |

*Primary Examiner*—Thurman K. Page
*Assistant Examiner*—William E. Benston, Jr.
*Attorney, Agent, or Firm*—Young & Thompson

[57] ABSTRACT

A method for making solid granules containing aromatic, nutritional, dietary or cosmetic substances, wherein a core consisting of excipients optionally combined with active substances is formed for use as a carrier, and the core is coated in three steps with at least one layer, with one layer being formed in each step, by (a) coating the core with active substances optionally combined with excipients, (b) drying the layer and (c) screening the coated core. The method is preferably used to make granules that contain plant extracts and essential oils and may be chewed, sucked, swallowed or dissolved.

10 Claims, No Drawings

PROCESS FOR THE PRODUCTION OF GRANULES, AND GRANULES THUS OBTAINED

FIELD OF THE INVENTION

The present invention has for its object an original manufacturing process for the production of granules whose size, color, solubility and active principles can vary according to the required final product: biogranules, aromatic granules, microgranules, pollen pearls, bath products. The assembly of these products will be better explained in the following:

So that the aromas of these products will be sufficiently present, it is necessary to use essential oils which are very volatile.

BACKGROUND OF THE INVENTION

FR-A-2,705,571 relates to the combination of two natural products, one being taken systematically as the base and is in the greater proportion: it is a fatty oil of animal or vegetable origin, the other is an aromatic essential oil extracted from a plant: *melaleuca alternifolia*, which can be replaced or associated with another aromatic essential oil of equivalent biochemical composition or conventionally known for its similar therapeutic effects, particularly on localized dental disorders: gum abscesses or any other paradontopathies having infectious or inflammatory characteristics.

FR-A-2,702,654 provides a cosmetic product permitting combatting and diminishing loose skin at the epidermis. It is constituted by an active mixture of essential oils incorporated in a vegetable oil. This product is particularly adapted to improve the texture of the skin.

These documents provide only liquid substances which are more difficult to store, preserve and use.

Moreover, in the present century in which poor lifestyle hygiene is often connected to undesirable eating habits, it is necessary to ingest natural and balanced products.

To do that, it is known to use vegetal extracts.

FR-A-2,662,078 has for its object a cosmetic composition. The composition according to this invention contains the following first materials: a mineral substance for external use called clay, which is white, yellow, red or green, according to its origin and the density of the metalloids or minerals that it contains, in a concentration of 70 to 80%; vegetal components, present in the form of plant flour and essential oils from plants, in a concentration of 18 to 19.5%; animal origin components, present in the form of homeopathic dilutions, so-called "opotherapies" (organo-therapy), in a concentration of 0.5 to 2%; in the composition ready to use, 100% of the first materials thus representing 46% of the final formula, 54% of added water; the vegetal components are marine algae, red grapevine, buttercup, cabbage, horsetail, and meadowsweet, to which are added essential oils of lavender, thyme or rosemary.

The mixture of the essential oils and the vegetal extracts are not very homogeneous amalgams. Moreover, the very volatile natural oils have a tendency to evaporate and the aroma to disappear.

FR-A-2,657,255 discloses obtaining new cosmetic products. These have the particularity of containing active principles in polymers which are themselves grafted on particles of silica.

WO-A-93/00991 relates to a process for the production of medical substances in the form of granules having a high apparent density, by depositing by pulverization a cladding on the particles with an inert core, with the help of a coating and granulating device by means of successive steps, first the constitution of a fluidized bed of particles of material with an inert core inside the treatment chamber of a cladding and granulating device, by causing to circulate a gaseous current between the rotating disc and the internal wall of said treatment chamber, then the constitution of the granules by means of depositing a medication on the particles of core material, cladding them by pulverization with a solution of medicament; the process being characterized by the fact that, during constitution of the granules, the particles clad by pulverization are first transported toward a drying zone surrounding the treatment chamber, secondly transported through said drying zone by a gas current and thirdly returned to the treatment chamber. The process of recirculation operates continuously until granules are constructed having the desired load of medication.

SUMMARY OF THE INVENTION

Generally speaking, it can be said that the characteristics which render the granules of the present invention original, compared to other cladding techniques, are the following:

Firstly, the assembly of the components used, active or excipient, constitute itself the starting core.

Secondly, the granule is thus homogenized in its composition, from the center to the outside, no matter what the size.

Thirdly, in the case of soluble granules, the granule is soluble totally (including the starting core) and the solubility (speed and medium) is a function of the components (quality and quantity) and of the excipients.

Fourthly, the granule permits integration and hence good conservation of the volatile components such as essential oils.

To this end, the present invention relates to a process for the production of solid granules adapted to provide products that can be chewed, sucked, swallowed or dissolved, containing aromatic substances, foodstuffs, dietetic substances, or substances for cosmetic use, characterized in that it consists:

in providing a core, serving as a support, constituted by excipients associated or not with active substances, the excipient or active principle is a solution which can for example be alcoholic, hydroalcoholic or aqueous, covering the core in three steps, with at least one layer, these three steps being carried out for each successive layer, by:

a) cladding the core with active substances associated or not with excipients, b) drying the layer, and c) screening the covered core.

This process is carried out under vacuum in at least one turbine rotating about an axis for cladding.

The axis of each rotating turbine is inclined at an angle of 45 to 60° relative to the horizontal.

The process is carried out at a temperature comprised between 18 and 25° C., except for drying which is carried out at a maximum of 45° C. in an oven.

It is carried out at a humidity less than 70%.

The granules, obtained by means of the above process, are characterized by the fact that they are each constituted of a central portion, forming the core, and a peripheral portion, forming one or several concentric layers; each layer is constituted by a component in solution and by a component in the form of a micronized powder.

On the one hand, the component in solution constitutes a cementing solution whose density is greater than that of water. On the other hand, the component, in the form of powder, constitutes a volumetric constituent.

The constituent in solution has a density comprised between 1010 and 1020 and a fluidity index comprised between 16 and 20.

DETAILED DESCRIPTION OF THE INVENTION

According to a first embodiment, the composition of the granules is substantially:

69% micronized maltisorb,
3.5% sodium bicarbonate,
3.5% citric acid,
21% concentrated fluid extract of plants, and
3% essential oils.

According to a second embodiment, the composition of the granules is substantially:

85% of a mixture of sodium bicarbonate and citrate,
10% of essential oils,
4% of emulgine, and
1% of luviskol.

No matter what the embodiment, the core has a diameter less than 0.01 mm, constituted of maltisorb or of a mixture of sodium bicarbonate and sodium citrate.

According to a particular embodiment, the core has a diameter substantially 2 mm constituted by pollen grains.

The present invention relates to a process for the production of granules of all shapes, sizes, etc.

The essence of the invention resides in the fact that this process is characterized by the fact that it consists in providing on the one hand a core serving as a support, and on the other hand, covering said core with at least one layer.

More precisely, the core is always constituted by excipients which can be or not associated with active substances. Similarly, each layer, which covers said core or a preceding layer disposed subjacently, is always formed from active substances which can be associated with excipients.

It is thus easy to understand that each layer which is deposited, will then be subjected to drying, and finally screening of the core covered by the dried layer.

These three steps, cladding, drying and screening, are each time carried out for each layer of product covering the core or a subjacent layer.

So that the granules will be formed in the most homogeneous way, there is used a stainless steel turbine which turns about an axis, itself inclined at an angle of 45 to 60° relative to the horizontal.

Moreover, the conditions within this turbine are very precise; thus, the temperature is always comprised between 18 and 25° C. except for drying during which the granules are ovened at 45° C. Moreover, the humidity must necessarily be lower than 70%, so as to avoid any amalgamation of the granules in a same turbine.

All the turbine production phase is carried out under an air flow of 2,500 m$^3$ per hour.

In fact, the granules which are provided by the process are thus constituted in a very homogeneous way from a central portion, forming the core, and a peripheral portion, formed by one or several concentric layers deposited according to the process.

The process requires the presence of three components having precise characteristics.

First of all the core, according to one preferred embodiment, is solid and in crystalline form or in crystals, and its diameter is less than 0.01 mm.

There is then an excipient or active principle component which is in solution, for example alcoholic, hydroalcoholic or aqueous, with a density which is greater than that of water. This component constitutes the binding solution.

Finally, there is also a component constituted also by an excipient or an active principle in the form of micronized powder. This latter component constitutes the volumetric component.

In any event, there is always at least one active principle among the three components.

The core and the volumetric component can be identical. The ideal density of the binding solution for practice of the process is 1010 for a fluidity index comprised between 16 and 20. Nevertheless, there can be a density comprised between 1010 and 1020.

As the case may be during preparation of the granules, it will be necessary to bring the solutions to the best density, either by concentration or by dilution, as a function of the characteristics of the substance and of its compatibility with the diluent.

The ratio between the binding solution of ideal density and the volumetric component is variable as a function of the final size of the product desired and of the density of the binding solution. But this remains fixed during all the duration of the production process.

According to a particular embodiment, the composition of the granules is substantially:

69% micronized maltisorb,
3.5% sodium bicarbonate,
3.5% citric acid,
21% concentrated fluid plant extract, and
3% essential oils.

According to another embodiment, the composition of the granules is substantially:

85% of a mixture of sodium bicarbonate and sodium citrate,
10% essential oils,
4% emulgine, and
1% luviskol.

According to another embodiment, the core may be constituted by agglomerated pollen grains and have a diameter of substantially two millimeters.

The assembly of these characteristics, which have been set forth, permits obtaining a range of products variable as to form, as a function of the manner of use. Thus, these granules can be used either by dissolving them or by chewing them or by swallowing them.

These three sets of figures are used, for example, for all instances of the ingestion of active substances. But there can be used granules which dissolve when it is desired to provide a solution such as an extract, a tea, a bath or an inhalation.

The different uses are of course due to the composition of the vegetal extracts and the essential oils which are used.

Among the substances that can be provided, there are biogranules of origin from a crystallized and calibrated maltisorb core. The fluid extracts and essential oils are deposited by pulverization.

When the fluid extracts are distributed uniformly over all the granules, the mask becomes binding and is worked only with difficulty in the turbine. The moisture contained in the core is absorbed by the addition of a certain quantity of mixture, thereby permitting free rotation. It suffices thus to let turn for several minutes with aspiration, so as totally to eliminate the alcohol contained in the hydro-alcoholic extracts, for example. Drying and screening follow to separate the granules of different sizes.

When the first layer is crystallized, a second layer is applied under the same conditions. The operation is then repeated to deposit, for successive layers, all of the aromatic principles. The quantity and form (solid or liquid) of the principle contained in each granule define the mean weight of each granule.

Another product is produced by the production of microgranules. This is in fact only a repetition of the biogranules, but with a smaller size. They can contain or not essential oils. The percentage of the components can vary as a function of the characteristics of solubility and of concentration of the required active principles.

Another product is constituted by vitamin pearls. In this case, the starting core is constituted by natural pollen grains which have already been set forth above.

After the calibration of granules two millimeters in size, the pollen cores are placed in the turbine and the technique which deposits the layers, as described above, is used.

Finally, the last product relates to bath products. In this case, the starting core and the volumetric component are constituted by a mixture of sodium bicarbonate and citric acid. The binding solution is constituted by essential oils, emulgine, luviskol and the coloring.

The production of course is carried out as previously given.

What is claimed is:

1. Process for the production of solid granules, containing substances selected from the group consisting of nutritional, pharmaceutical, and cosmetic substances, which comprises:

providing a solid core consisting of at least one excipient optionally associated with active substances for use as a support, the excipient or active principle being in solution, covering the core, in three steps, with at least one layer, the three steps being carried out for each successive layer, by:

a) coating the core with active substances optionally associated with excipients, said coating being carried out under vacuum in at least one turbine rotating about an axis, b) drying the layer, and c) screening the core covered by the dried layer to obtain the solid granules;

said process being carried out at a humidity of less than 70%, and at a temperature comprised between 18 and 25° C., except for the drying step which is carried out at a maximum temperature of 45° C. in an oven.

2. Process according to claim 1, wherein the axis of each rotating turbine is inclined at an angle of 45 to 60° relative to the horizontal.

3. Solid granules, obtained by the process according to claim 1, wherein each granule comprises a central portion forming the core, and a peripheral portion forming one or several concentric layers; each layer comprising a component in solution and a component in the form of micronized powder.

4. Granules according to claim 3, wherein the component in solution is a binding solution whose density is greater than water, and the component in the form of a powder is a volumetric component.

5. Granules according to claim 3, wherein the component in solution has a density ranging between 1010 and 1020 and a fluidity index ranging between 16 and 20.

6. Granules according to claim 3, wherein the composition of the granules is substantially:

69% of micronized maltisorb, 3.5% of sodium bicarbonate, 3.5% of citric acid,

21% of fluid concentrated plant extract and

3% of essential oils.

7. Granules according to claim 3, wherein the composition of the granules is substantially:

85% of a mixture of sodium bicarbonate and sodium citrate,

10% of essential oils,

4% of emulgine, and

1% of luviskol.

8. Granules according to claim 6, wherein the core has a diameter smaller than 0.01 mm, constituted by maltisorb.

9. Granules according to claim 7, wherein the core has a diameter smaller than 0.01 mm, constituted by a mixture of sodium bicarbonate and sodium citrate.

10. Granules according to claim 3, wherein the core has a diameter of about 2 mm constituted by pollen grains.

* * * * *